(12) United States Patent
Phillips (10) Patent No.: US 7,060,104 B2
(45) Date of Patent: Jun. 13, 2006

(54) ENERGY STORING FOOT PROSTHESIS WITH IMPROVED PLANTAR FLEXION

(76) Inventor: Van L. Phillips, 33000 Navarro Ridge Rd., Albiou, CA (US) 95410

( * ) Notice: Subject to any disclaimer, the term of this patent is extended or adjusted under 35 U.S.C. 154(b) by 0 days.

(21) Appl. No.: 10/410,713

(22) Filed: Apr. 9, 2003

(65) Prior Publication Data
US 2003/0191541 A1    Oct. 9, 2003

Related U.S. Application Data

(63) Continuation of application No. 09/945,092, filed on Aug. 30, 2001, now abandoned.

(60) Provisional application No. 60/229,113, filed on Aug. 30, 2000.

(51) Int. Cl.
*A61F 2/66* (2006.01)

(52) U.S. Cl. .......................................... 623/55; 623/49

(58) Field of Classification Search ............... 623/49, 623/52, 53, 54, 55, 56
See application file for complete search history.

(56) References Cited

U.S. PATENT DOCUMENTS

| | | | |
|---|---|---|---|
| 2,075,583 A | 3/1937 | Lange | |
| 2,453,969 A | 11/1948 | Carter | |
| 2,470,480 A | 5/1949 | Fogg | |
| 2,640,200 A | 6/1953 | Wisbrun | |
| 3,335,428 A | 8/1967 | Gajdos | |
| 3,551,914 A | 1/1971 | Woodall | |
| 3,874,004 A | 4/1975 | May | |
| 4,547,913 A | 10/1985 | Phillips | |
| 4,645,509 A | 2/1987 | Poggi et al. | |
| 4,721,510 A | 1/1988 | Cooper et al. | |
| 4,822,363 A | 4/1989 | Phillips | |
| 5,019,109 A | 5/1991 | Voisin | |
| 5,037,444 A | 8/1991 | Phillips | |
| 5,112,356 A | 5/1992 | Harris et al. | |
| 5,116,384 A | 5/1992 | Wilson et al. | |
| 5,181,932 A | 1/1993 | Phillips | |
| 5,290,319 A | 3/1994 | Phillips | |
| 5,387,246 A * | 2/1995 | Phillips | 623/56 |
| 5,507,838 A | 4/1996 | Chen | |
| 5,514,185 A | 5/1996 | Phillips | |
| 5,549,711 A | 8/1996 | Bryant | |

(Continued)

OTHER PUBLICATIONS

Shipping invoice (labeled "A") for prototype shipped outside U.S. for testing purposes more than one year before the Aug. 30, 2000 priority date of the present application; dates and addresses redacted (Ski leg).

(Continued)

*Primary Examiner*—Bruce E. Snow
(74) *Attorney, Agent, or Firm*—Knobbe, Martens, Olson & Bear, LLP.

(57) ABSTRACT

A prosthetic foot characterized by an easily exchangeable auxiliary ankle member demountably attached to forefoot and sole portions, which are in turn demountably and interchangeably connected. The forefoot, heel and auxiliary ankle portions are fabricated from polymer impregnated and encapsulated laminates, including such laminates as carbon fibers and/or fiberglass or synthetic fibers such as Kevlar. The easily demountable connection of the auxiliary ankle permits interchangeability thereof to match the activity schedule of the wearer utilizing the prosthetic foot without the necessity of frequent visits to the prosthetist. A compressible member between the forefoot member and the sole member, and function blocks located between the various members provide additional adjustability. The orientation of the auxiliary ankle member and compressible member also allows for increased plantar flexion.

31 Claims, 5 Drawing Sheets

U.S. PATENT DOCUMENTS

| | | | |
|---|---|---|---|
| 5,653,767 | A | 8/1997 | Allen et al. |
| 5,899,944 | A | 5/1999 | Phillips |
| 5,944,760 | A * | 8/1999 | Christensen ............. 623/55 |
| 6,071,313 | A | 6/2000 | Phillips |
| 6,241,776 | B1 | 6/2001 | Christensen |

OTHER PUBLICATIONS

Shipping invoice (labeled "B") for prototype shipped within U.S. for testing purposes more than one year before the Aug. 30, 2000 priority date of the present application; dates and addresses redacted (Ski leg).

Shipping invoice (labeled "C") for prototype shipped outside U.S. for testing purposes more than one year before the Aug. 30, 2000 priority date of the present application; dates and addresses redacted (Ski leg).

Shipping invoice (labeled "D") for prototype shipped outside U.S. for testing purposes more than one year before the Aug. 30, 2000 priority date of the present application; dates and addresses redacted (Ski leg).

Shipping invoice (labeled "E") for prototype shipped within U.S. for testing purposes more than one year before the Aug. 30, 2000 priority date of the present application; dates and addresses redacted (Ski leg).

* cited by examiner

ENERGY STORING FOOT PROSTHESIS WITH IMPROVED PLANTAR FLEXION

CROSS-REFERENCE TO RELATED APPLICATIONS

This application is a continuation of U.S. application Ser. No. 09/945,092, filed Aug. 30, 2001 now abandoned, which claims the benefit of U.S. Provisional Application No. 60/229,113, filed Aug. 30, 2000, the entirety of each one of which is hereby incorporated by reference herein.

BACKGROUND OF THE INVENTION

1. Field of the Invention

This invention relates to foot prostheses in general, and specifically to a prosthetic foot characterized by a unitary foot and heel construction, and an auxiliary ankle construction which permits the flexibility of the prosthesis to be selectively determined and easily changed.

2. Background of the Invention

Although many prosthetic devices have attempted to simulate the ambulation of a normal foot, very few of them are readily adjustable in terms of their performance characteristics. Adjustability is especially desirable among amputees who frequently participate in a variety of physical activities requiring varying levels of energy-storing and -releasing attributes.

Certainly, some prior art devices more nearly achieve the desired ease of adjustability than do others. For example, see my U.S. Pat. No. 4,547,913 for my invention relating to a "Composite Prosthetic Foot and Leg," U.S. Pat. No. 4,822,363 for my invention relating to a "Modular Composite Prosthetic Foot and Leg," my U.S. Pat. No. 5,181,932 for my invention relating to a "Foot Prosthesis Having Auxiliary Ankle Construction" and U.S. Pat. No. 5,290,319 for my invention relating to a "Prosthetic Foot Incorporating Adjustable Bladders" Also my U.S. Pat. Nos. 5,037,444 and 6,071,313 discloses a prosthetic foot device with similar preferred materials and methods of manufacture, and with corresponding benefits therefrom. Each of these patents is incorporated by reference herein.

Notwithstanding the valuable contribution and characteristics of my aforementioned patented foot prostheses and specifically the modularity thereof, the adjustment of those prostheses is relatively involved. Any adjustment of the performance characteristics of those prostheses basically requires the disassembly of a covering shroud (if present) and of structural members from each other and specifically from the pylon tube (through bolt, nut, and washer combinations, for example). After a new combination of structural members has been selected, it typically must similarly be reassembled. Disassembly of the prosthetic foot from the pylon requires a significant amount of time, effort, and money as it must be done by a prosthetist.

Other prosthetic foot devices are even less readily adjusted, and include U.S. Pat. No. 3,335,428 to Gajdos, which attempts to duplicate the skeletal and skin structure of a natural human foot, U.S. Pat. No. 2,075,583 to Lange, which incorporates a rubber form mounted in operative relationship with a rigid metallic core, and U.S. Pat. No. 4,645,509 to Poggi, which teaches a prosthetic foot incorporating a monolithic keel or beam of relatively massive proportions intended to react to the load of an amputee's body during walking, running, jumping, and the like and to release the resultant stored energy to create foot lift and thrust complementing the amputee's natural stride.

Moreover, the dynamic performance of many of these other prior art devices is relatively stiff and immediate, and generally cannot produce adequate plantar flexion during heel strike, while retaining sufficient stiffness for toe-off.

SUMMARY OF THE INVENTION

It is, therefore, one object of my invention to provide a foot-prosthesis which can be easily adjusted without the necessity of removing the foot from the vertical pylon of an amputee's prosthetic leg. This will allow an active amputee to participate in a wide variety of activities without the necessity of frequent visits to the prosthetist.

In one embodiment, the present invention provides a foot prosthesis characterized by an easily removable auxiliary support member, herein also termed an auxiliary ankle or second foot portion, in conjunction with a primary support member, herein termed the forefoot member or first foot portion, and a lower support member, herein termed the sole member or third foot portion. The primary and lower support members are of such character as to be easily adaptable to provide size adjustment or accommodation of different spring rates to suit the size of foot, or of the stride and weight of the amputee. The auxiliary support member provides further adjustment to accommodate varying activity levels of a given amputee. The ease of removal of the auxiliary support member provides a degree of quick and easy adjustment previously unobtainable with prior prosthetics.

These members are preferably fabricated, for example, from polymer impregnated and encapsulated laminates, including such laminates as carbon fibers and/or fiberglass or synthetic fibers such as Kevlar. Such members provide desirable energy-storing and —releasing characteristics.

Another object of the invention is the incorporation in a prosthetic foot of the aforementioned character of compressible members in order to achieve a gradual dynamic transition, which can further improve the degree of adjustability of the prosthesis.

The particular location of attachment of the auxiliary support member allows for increased performance. Plantar flexion can be increased by not limiting the flexibility of the forefoot portion during heel strike, yet the ankle portion is still stiffened by the auxiliary support member during toe off. The inclusion of compressible members disposed between the auxiliary support member, and the forefoot member allows for further adjustability of performance characteristics.

Other objects and advantages of the invention will be apparent from the following specification and the accompanying drawings, which are for the purpose of illustration only.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and its essential features and advantages, certain preferred embodiments and modifications thereof will become apparent to those skilled in the art from the detailed description herein having reference to the figures that follow, of which.

DETAILED DESCRIPTION OF THE PREFERRED EMBODIMENTS

Figure 1:
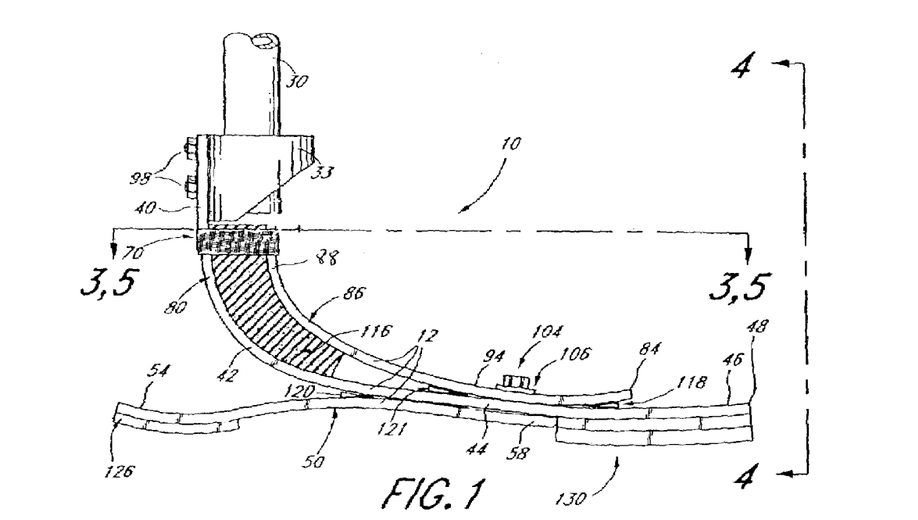
FIG. 1 is a side elevation view of one preferred embodiment of a prosthetic foot.

Referring to the drawings, and particularly to FIG. 1, I show one preferred embodiment of a foot prosthesis 10 constructed in accordance with the teachings of the invention. The foot 10 generally includes a forefoot member 80, a sole member 50, and an auxiliary support member 86 operatively and demountably attached to each other at the arch section 44. Attachment is preferably accomplished using suitable nut and bolt combinations 104 associated with a load-transmitting metallic plate 106. The auxiliary member is preferably attached to the forefoot member such that the auxiliary member may add to the stiffness of the ankle portion of the forefoot member. If desired, a retaining band 70 may be provided at the ankle section 42. A compressible member 116 may be provided between the auxiliary member, and the forefoot member. Function blocks 118, 120, 121, and 119 (FIG. 2) may also be provided in order to vary the length of the effective lever arms of the various members. If indicated, the forefoot and sole portions can be permanently secured to each other, as by epoxy adhesive, a polyurethane resilient layer, or the like.

The forefoot member 80 preferably includes a substantially rigid upper attachment section 40, a forward and downward curving ankle section 42, an arch section, 44, and a distal toe section 46. The sections 40, 42, 44, and 46 are preferably formed integrally with one another and simultaneously by the incorporation of a plurality of laminae embedded in a hardened, flexible polymer.

In the particular embodiment shown, the sole member 50 includes an attachment section 58 and a heel section 54 extending substantially rearward from said attachment section 58. The sections 58 and 54 are preferably formed integrally with one another and simultaneously by the incorporation of a plurality of laminae embedded in a hardened, flexible polymer as described herein.

The auxiliary support member 86 includes a lower section 94 and an upper section 88. Said lower section 94 of the auxiliary support member 86 is rigidly attached to said forefoot member 80 and said sole member 50 with nut and bolt combinations 104, and extends substantially rearward and upward, its uppermost edge 88 preferably terminating below said attachment section 40 of said forefoot member 80.

Figure 2:
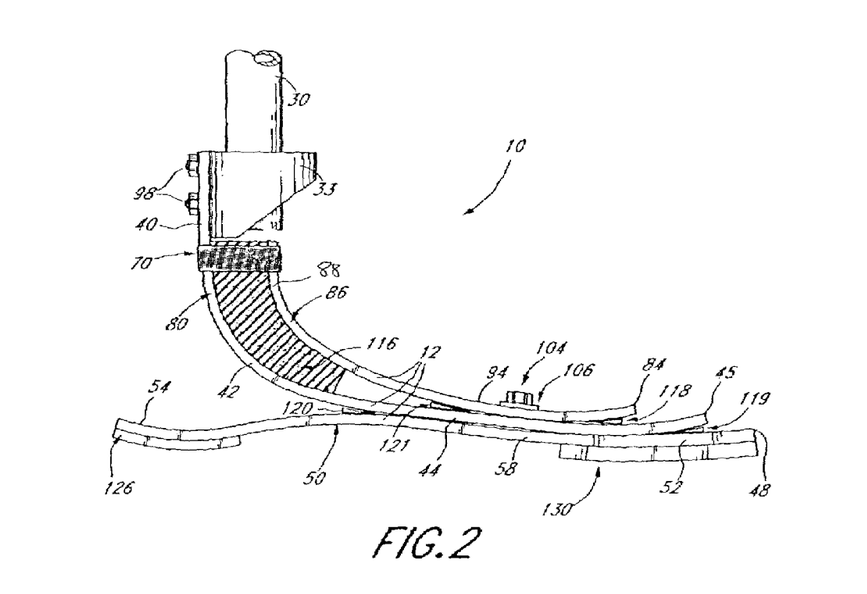
FIG. 2 is a side elevation view of an alternative embodiment of a prosthetic foot.
Figure 3:
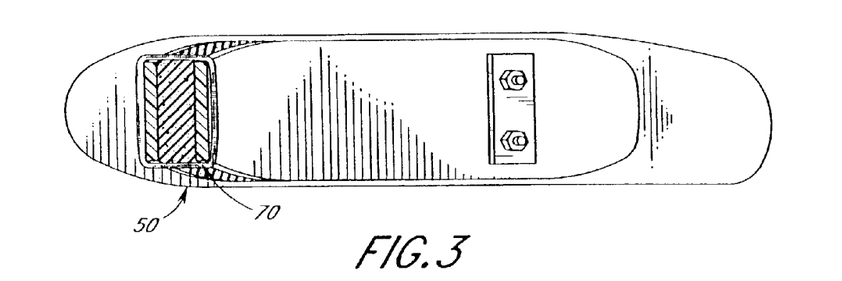
FIG. 3 is a top view of the foot of FIG. 1.

In an alternative embodiment, shown in FIG. 2, the sole member 50 extends substantially forward from said attachment section to the forwardmost tip 48 of the foot 10, and the forefoot member 80 preferably extends slightly forward from the forwardmost tip 84 of the auxiliary support member 86, curving slightly upwards to a distal tip 45. In this alternative embodiment, a block 119 can be interposed between the tip 45 of the forefoot portion 80, and the toe section 52 of the sole member 50.

Resilient blocks of wedge-shaped configuration and of various size may be included, for example in the positions indicated in the drawings as 118, 120, 121, and 119, FIG. 2, such that they allow for the variability of the lever arms of the structural members 80, 86, and 50. For example FIG. 1 shows a block 118 interposed between the under surface of the forward portion 84 of the auxiliary ankle 86 and the upper surface of the arch section 44 of the forefoot member 80, which has the effect of decreasing the lever arm of the toe portion 46 of the forefoot member 80.

Figure 4:
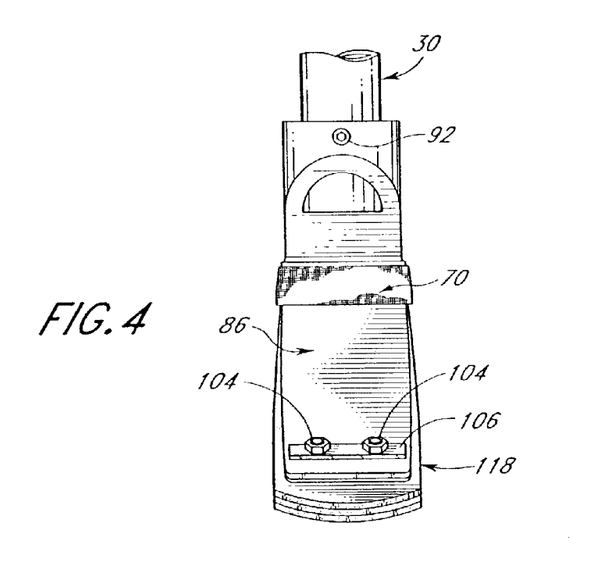
FIG. 4 is a front elevation view of the foot of FIG. 1.

The attachment section 40 of the forefoot member 80 preferably incorporates two centrally-located openings (not shown). The attachment section 40 is substantially rigid and capable of sustaining torsional, impact and other loads impressed thereupon by the toe portion 46 and heel portion 54 of the prosthesis. In addition, the inherent rigidity of the attachment section 40 causes the effective transmission of the aforesaid loads imposed thereupon to a suitable ancillary prosthetic pylon 30, by bolt and nut combinations 98 assembled through the two openings (not shown, as mentioned above) to a pylon coupling 33. A screw 92 (FIG. 4) or other suitable attachment means secures the ancillary pylon 30 in the coupling 33. Those skilled in the art will recognize that a variety of other attachment means may be utilized, such as glue, rivets, tape, etc.

Figure 5:
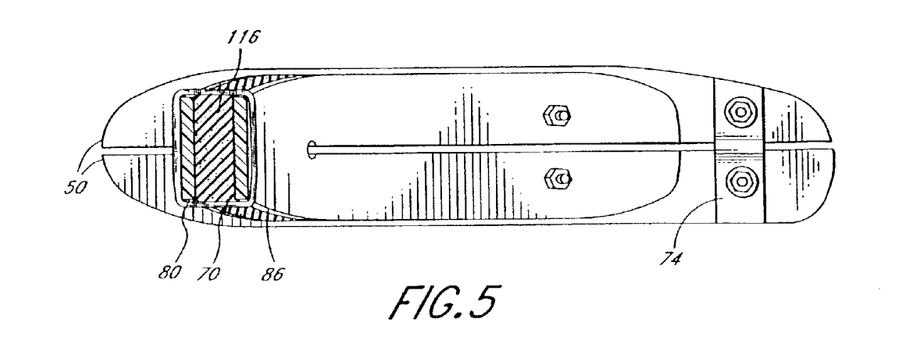
FIG. 5 is a top view of an alternative embodiment of a prosthetic foot.
Figure 6:
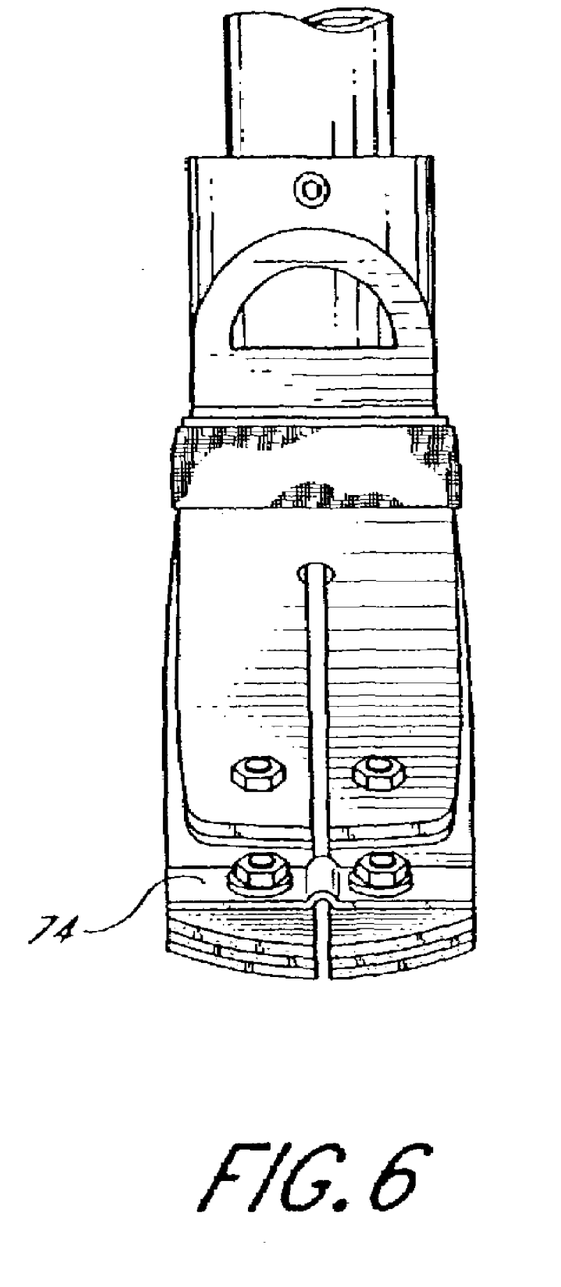
FIG. 6 is a front elevation view of the foot of FIG. 5.

In an alternative embodiment shown in FIGS. 5–6, the sole member 50 and part of the forefoot portion 80 are bifurcated into multiple side-by-side foot portions such that they are capable of movement independent from one another. Preferably, the foot is bifurcated by the provision of a slot in said forefoot and sole portions. A strap 74 or similar expedient may be provided to limit the movement of the side-by-side foot portions relative to each other, if desired. The auxiliary ankle member described herein would also be preferably included in this embodiment. The concept of the split foot is described in detail in my U.S. Pat. No. 6,071,313 which is incorporated herein by reference.

Figure 7:
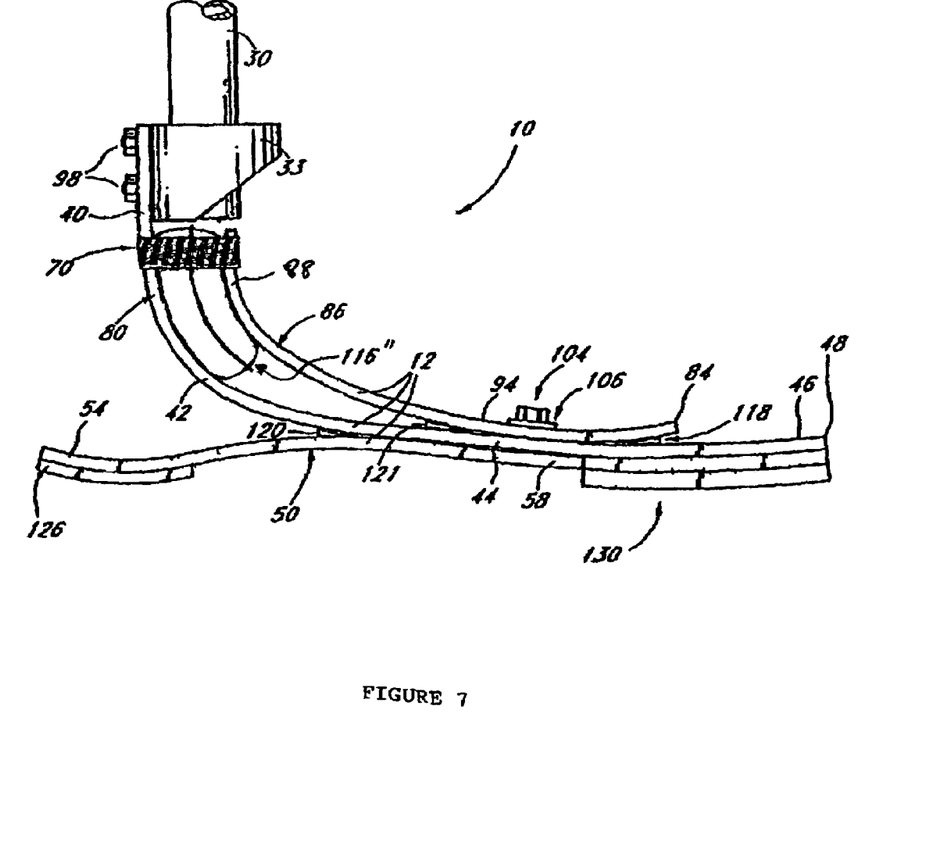
FIG. 7 is a side elevation view of an alternative embodiment of a prosthetic foot.

A compressible member 116 may be disposed between said forefoot member 80 and said auxiliary support member 86. The compressible member 116 is preferably fabricated such that it provides additional adjustment of the performance characteristics of the prosthesis 10 through the variation of its degree of compressibility. For example, an inflatable bladder 116' of FIG. 7 filled with air, $CO_2$ or other gas could be used. In a particularly preferred embodiment of the present invention the compressible member 116 may comprise a compressible foam member. A foam member provides a low-cost compressible member for energy storage and release, and avoids the inherent potential difficulties of air bladders such as leakage and risk of puncture. The foam member also provides a slight dampening of the prosthetic foot which improves the overall response characteristics and provides a more natural feeling foot.

The compressible member 116 may be molded or fabricated from a wide variety of resilient materials, as desired, such as natural or synthetic rubber, plastics, polyurethane, honeycomb structures or any one of a variety of other materials well known to those skilled in the art for storing and releasing energy. Cellular foam is preferred to provide a desirable spring characteristic and a more natural stride. For example, expanded polyurethane such as cellular Vulkolka PUR-CELL No. 15-50 with a density of approximately 500 kilograms per cubic meter, available from Pleiger Plastics Company of Washington, Pa., may be used to form the compressible member 116. Foam densities of between about 150 and 1500 kg/m³ may also be used to obtain the benefits of the invention taught herein.

The rear surface of the auxiliary ankle member 86 is preferably allowed to slip relative to the compressible member 116 in order to allow for increased plantar flexion. The compressible member 116 may be held in place by glue, velcro, snaps, or a variety of other methods as recognized by one skilled in the art such that the preferred slipping between the auxiliary ankle member 86 and the compressible member 116 is allowed.

Figure 8:
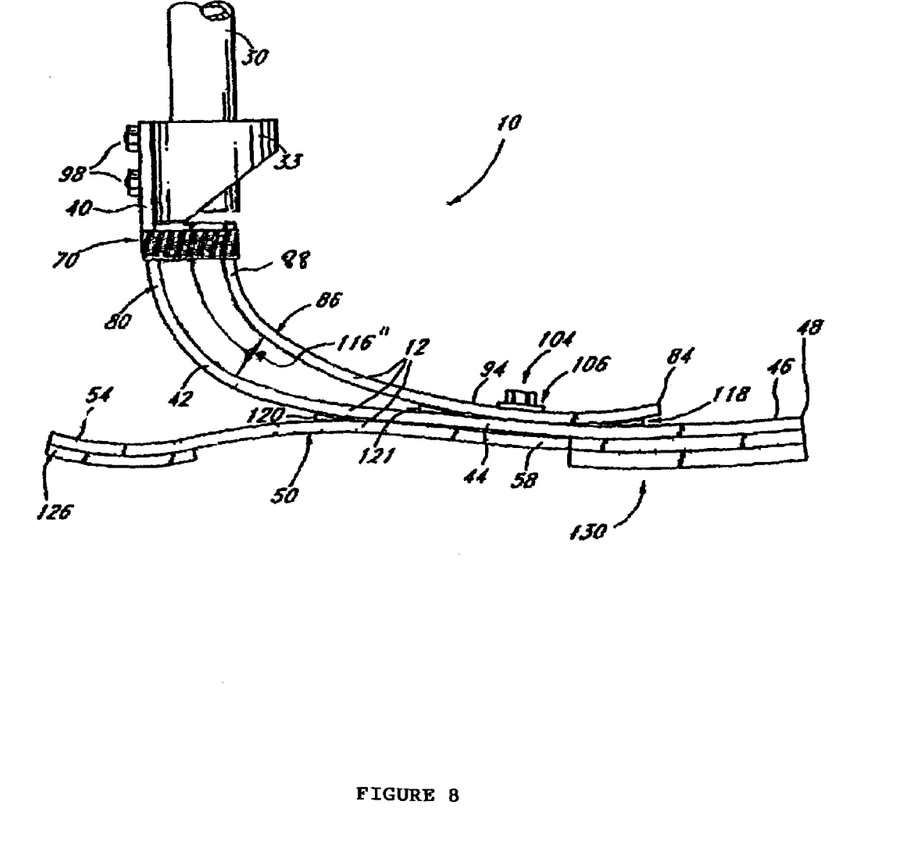
FIG. 8 is a side elevation view of an alternative embodiment of a prosthetic foot.

Alternatively, the compressible member 116 may be replaced by a substantially non-compressible friction-reducing element 116" of FIG. 8, or eliminated altogether. The absence of the compressible member 116 would cause the wearer to experience more resistance to motion during toe-off, while its presence allows for slower, more gradual resistance during toe-off. Either or both of these cases may be desirable depending on the activity for which the foot is needed.

Toe pads 130 and/or a heel pad 126 may be disposed under the toe section 46 of the forefoot member 80 and the heel section 54 of the sole member 50 respectively, so as to provide minor shock absorption to the prosthetic 10.

In the preferred embodiment, bolt and nut combinations 104, in conjunction with the load-distributing metallic plates 106, serve to secure the sole member 50 in operative relationship with the forefoot member 80 of the prosthesis. This mode of affixation facilitates the assembly or dismounting of selected sole members 50 in operative relationship with selected forefoot members 80, thus permitting a wide range of different sizes and stress load response characteristics to be related to each other to accomplish the optimum functional correspondence between the primary and sole portions 80 and 50.

The auxiliary ankle member 86 provides further adjustability of the performance characteristics of the prosthetic 10 by adding to the stiffness of the forefoot member 80. The auxiliary ankle 86 is formed from fibrous laminates of the same character as the various portions of the prosthesis 10. In a preferred embodiment of the present invention, the auxiliary ankle 86 incorporates an attachment section 94 which is operatively associated with the ankle section 42 of the forefoot member 80 and the attachment section 58 of the sole member 50.

The auxiliary ankle 86 is preferably secured in operative relationship with the curvilinear ankle section 42 of the forefoot member 80 through the aforementioned assembly of the bolt and nut combinations 104. On its end opposite from the attachment section 94, ankle member 86 has an upper section 92 which is preferably fixed in operative relationship with a compressible member 116 and the curvilinear ankle section 42 of the forefoot member 80 by the use of a flexible, yet substantially non-stretching strap 70. Said compressible member 116 providing a gradual dynamic transition throughout toe-off.

The strap 70 may be fabricated from a suitably tough, flexible material such as impregnated canvas or the like, and is configured and assembled with the ankle section 42 of the forefoot member 80, the auxiliary support member 86, and/or the compressible member 116 to achieve desired stress-storage and -release performance in the prosthesis. For example, the strap 70 may be releasably attached around the auxiliary support member 86 through the provision of Velcro-type fasteners or similar expedient.

A restraining element such as the strap 70 may be incorporated at various locations on the prosthesis 10 to restrict the distance that associated structural members 86, 80, and 50 may move from one another in order to control the performance characteristics of said foot. For example, one skilled in the art will recognize that increased distance of motion between the auxiliary support member 86 and forefoot member 80 during heel strike will allow for increased plantar flexion. The retaining element may be utilized to prevent undesirable excessive loading and stressing of a particular member 86, 80, or 50, and/or to combine the spring-stress response characteristics of the associated structural members 12 under certain loading conditions. For example, the strap 70 as assembled in FIG. 1 permits the auxiliary member 86 to assist in raising the toe 46 of the prosthesis 10 and to store and release spring energy when the heel portion 54 is struck on the ground in front of the wearer. The retaining element may be either substantially elastic and stretchable, or substantially static and non-stretchable, depending on the degree of relative motion desired.

In the preferred embodiment, the auxiliary ankle member 86 is secured against the relatively concave surface of the curvilinear ankle section 42, so that the anticipated upward deflection of a toe section 46 of the forefoot member 80, as more thoroughly described below, will eventually cause deformation of the auxiliary ankle 86 as well as deformation of the ankle section 42, effectively combining the deformation resistance and energy storage characteristics of the auxiliary ankle member 86 with those of the forefoot member 80. Alternative embodiments would include securing the auxiliary ankle 86 to the underside of the arch section 44 and continuing to use the strap 70 to maintain the functional relationship between the auxiliary ankle 86 and the forefoot member 80 in order to achieve the aforedescribed desired combination of the deformation resistance and energy storage characteristics of the auxiliary ankle member 86 with those of the ankle section 42.

The auxiliary ankle member 86 can be provided with different numbers of laminates to make it more or less compliant to loads transmitted through the forefoot member 80. Consequently, when confronted with various anomalies in an amputee, such as overweight or excess activity levels, the basic structure of the forefoot member 80, and more particularly the ankle section 42, can be materially modified to provide ankle portion action which is precisely adjusted to the needs of the amputee. Moreover, a variety of auxiliary ankle members 86 can be made available to an active amputee, allowing the flexibility of the prosthesis to be adjusted on the basis of the particular activity which the amputee is undertaking. Furthermore, the location of the point of attachment at the arch section 44 allows exchange of auxiliary ankle sections 86 to be made without necessarily removing the prosthesis 10 from the pylon 30.

A cosmetic cover (not shown) can be provided to shroud the prosthesis 10 after the optimum assemblage of the primary and sole members 80 and 50 and an auxiliary ankle member 86 has been accomplished. The cosmetic cover, which may be formed of low-density formed polymer, is not required to serve any ancillary shock-absorbing or other stress-isolating function since all of the loads imposed upon the prosthesis can be absorbed, transmitted and reasserted in a manner to be described in greater detail below.

The materials from which the forefoot member 80, sole member 50, and the auxiliary ankle 86 are formed preferably possess the ability to provide an energy-storing, resilient, spring-like effect. This is preferred because each engagement of the prosthesis 10 with an adjacent surface impresses compression, torsional and other loads upon the prosthesis 10 which are stored within the prosthesis and then, dependent upon the stride of the wearer, re-impressed upon said surface to achieve a natural stride conforming, ideally, in all respects to the stride of the unimpaired limb of the wearer of the prosthesis 10.

These members are preferably fabricated, for example, from polymer impregnated and encapsulated laminates. To achieve the relatively thin construction of the forefoot and sole members 80 and 50 and the auxiliary support member 86 of the prosthesis 10, the aforesaid polymers are utilized in conjunction with various laminating materials. Various types of fibrous laminae can be utilized to achieve the continuum required by the design of the forefoot and sole members 80 and 50 and the auxiliary support member 86 to complement the stress-absorbing and storing characteristics of the polymers in which said fibrous laminae are embedded.

Of course, there is a wide variety of fibrous reinforcements in the form of laminae available at the present time, including such inorganic fibers as glass or carbon fibers. These inorganic fibers are customarily provided in tape or sheet form and can be readily superimposed in the mold to permit them to be encapsulated in the selected polymer.

Obviously, the number of superimposed laminae and the lengths thereof, together with the thickness of the encapsulating polymer, determine the stress characteristics of the resultant forefoot and sole members 80 and 50 and the auxiliary support member 86 and, correspondingly, determine the total weight of the prosthesis 10. As will be apparent from the discussion herein, the forefoot and sole members 80 and 50 and the auxiliary support member 86 are designed to specifically accommodate individuals having different foot sizes, different weights and different strides and the individual design of the forefoot and sole members 80 and 50 and the auxiliary support member 86 provides for matching, to an extent previously unknown in the art, the natural characteristics of the wearer's uninjured limb.

Furthermore, the function blocks 118, 120, 121 and 119, FIG. 2 can be provided in different sizes and in materials having different compression characteristics so that the respective lever arms and the corresponding deflections of the heel section 54 and the toe section 46 or 52 may be increased or decreased.

It will be understood by those of skill in the art that the terms such as ankle, heel portion, arch and forefoot portion are used herein as convenient references to describe the general function and/or location of the various portions of the prosthesis and are not intended to indicate that the prosthesis has a structural configuration replicating these anatomical structures of the human foot.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A prosthetic foot comprising:
   a first foot portion capable of supporting an amputee, and of providing energy storage and release, said first foot portion having a substantially vertical attachment section, an intermediate curvilinear ankle section curving at least substantially downward from said attachment section, and a lower section extending substantially forward from said ankle section, said attachment section being securable to a pylon member, socket or other prosthetic leg member intermediate said foot and a stump of the amputee; and
   a second foot portion having an upper section and a lower section, said second foot portion being immovably secured relative to said first foot portion at said lower section thereof to said lower section of said first foot portion, said second foot portion extending substantially rearward and upward from said lower section of said second foot portion generally along said first foot portion, said upper section terminating substantially near said attachment section of said first foot portion and spaced a distance therefrom;
   wherein said first foot portion and said second foot portion are separated by a gap adjacent the vertical attachment section and the upper section.

2. The prosthetic foot of claim 1 additionally comprising a third foot portion having an attachment section and a heel section, said attachment section of said third foot portion being secured with said first foot portion at a point along said lower section of said first foot portion, said third foot portion extending substantially rearward.

3. The prosthetic foot of claim 1 wherein a restraining element is used to limit the movement of one portion of said foot relative to another portion.

4. The prosthetic foot of claim 3 wherein said restraining element is a strap of substantially flexible and non-stretchable material.

5. The prosthetic foot of claim 3 wherein said restraining element is a strap of substantially flexible and stretchable material.

6. The prosthetic foot of claim 1 additionally comprising a substantially non-compressible element of friction-reducing material disposed between said second foot portion and said first foot portion.

7. The prosthetic foot of claim 1 additionally comprising a resilient compressible member disposed between said second foot portion and said first foot portion, said compressible member being fabricated from a compressible foam.

8. The prosthetic foot of claim 1 additionally comprising a resilient compressible member disposed between said second foot portion and said first foot portion, wherein said compressible member comprises an inflatable bladder.

9. The prosthetic foot of claim 1 having a lower surface and additionally comprising one or more compressible pads disposed on the lower surface of said foot such that they provide cushioning to said foot during use by the amputee.

10. The prosthetic foot of claim 1 additionally comprising a resilient, compressible block disposed between said lower section of said second foot portion and said toe section of said first foot portion such that said block will be compressed during toe-off.

11. A prosthetic foot comprising:
a primary support member capable of supporting an amputee, and of providing energy storage and release, said primary support member having a substantially vertical attachment section, an intermediate curvilinear ankle section curving at least substantially downward from said attachment section, an arch section extending substantially forward from said ankle section, and a toe section extending substantially forward from said arch section, said attachment section being securable to a pylon member, socket or other prosthetic leg member intermediate said foot and a stump of the amputee;
an auxiliary support member positioned forward of said primary support member and having an upper section, an intermediate section, and a lower section, said auxiliary support member secured directly against said primary support member at a point on the lower section of said auxiliary support member, said auxiliary support member extending rearward and upward from said lower section substantially along said primary support member, said upper section terminating near said attachment section of said primary support member; and
a lower support member having a central attachment section, a heel section extending substantially rearward from said attachment section, and a toe section extending substantially forward from said attachment section, said toe and heel sections providing lever arms for said foot, said attachment section of said lower support member being secured with said auxiliary support member and said primary support member at a point along said arch section of said primary support member;
whereby said second foot portion can be easily removed and exchanged without removing said foot from said prosthetic leg member.

12. The prosthetic foot of claim 11 wherein a restraining element is used to limit the movement of one member of said foot relative to another member.

13. The prosthetic foot of claim 12 wherein said restraining element is a strap of substantially flexible and non-stretchable material.

14. The prosthetic foot of claim 12 wherein said restraining element is a strap of substantially flexible and stretchable material.

15. The prosthetic foot of claim 11 additionally comprising a resilient compressible member disposed between said auxiliary support member and said primary support member, said compressible member comprising compressible foam.

16. The prosthetic foot of claim 11 additionally comprising a resilient compressible member disposed between said auxiliary support member and said primary support member, wherein said compressible member comprises an inflatable bladder.

17. The prosthetic foot of claim 11 comprising a substantially non-compressible friction-reducing element disposed between said auxiliary support member and said-primary support member.

18. The prosthetic foot of claim 11 additionally comprising one or more compressible pads disposed on the lower surface of said foot such that they provide cushioning to said foot during use by the amputee.

19. The prosthetic foot of claim 11 additionally comprising a resilient, compressible block disposed between said lower section of said auxiliary support member and said toe section of said primary support member such that said block will be compressed during toe-off.

20. The prosthetic foot of claim 11 wherein said arch section of said primary support member terminates in an upward-curving tip above said toe section of said lower support member, wherebetween a substantially resilient, compressible control block is disposed, and additionally comprising a substantially resilient, compressible control block disposed between said lower section of said auxiliary support member and said primary support member such that said blocks would be compressed during toe-off.

21. A prosthetic foot, comprising:
a resilient primary support member for attachment to an artificial leg and having a lower end;
a sole member separately attached to said primary support member, said sole member being generally horizontal over substantially its entire length; and
a stiffening member removably attached to a point substantially near the lower end of said primary support member such that it alters the resilience of said primary support member;
wherein the sole member and the stiffening member are immovably attached to the primary support member at the same location to prevent motion of the sole member, stiffening member, and primary support member relative to each other;
wherein said stiffening member terminates at an upper end at a termination point spaced from said primary support member.

22. The prosthetic foot of claim 1 wherein said second foot portion can be removed and exchanged without removing said foot from said prosthetic leg member.

23. The prosthetic foot of claim 1 additionally comprising a toe section extending substantially forward from said lower section of said first foot portion.

24. The prosthetic foot of claim 23 wherein said toe section provides a lever arm for said foot.

25. The prosthetic foot of claim 2 wherein bending stress is distributed substantially evenly throughout said third foot portion during heel strike.

26. The prosthetic foot of claim 2 wherein said heel section of said third foot portion provides a lever arm for said foot.

27. The prosthetic foot of claim 1 wherein said second foot portion is directly secured at said lower section thereof to said lower section of said first foot portion.

28. The prosthetic foot of claim 27 wherein said second foot portion is directly secured at said lower section thereof to said lower section of said first foot portion with a bolt.

29. The prosthetic foot of claim 1 further comprising:
a resilient member disposed between the first foot portion and second foot portion;
wherein energy storage and return characteristics of the resilient member are adapted to be modified, to thereby provide the foot with variable stiffnesses.

30. The prosthetic foot of claim 11 further comprising:
a resilient member disposed between the primary support member and auxiliary support member;
wherein energy storage and return characteristics of the resilient member are adapted to be modified, to thereby provide the foot with variable stiffnesses.

31. The prosthetic foot of claim 21 further comprising:
a resilient intermediate member disposed between the resilient primary support member and stiffening member;
wherein energy storage and return characteristics of the resilient intermediate member are adapted to be modified, to thereby provide the foot with variable stiffnesses.

* * * * *

UNITED STATES PATENT AND TRADEMARK OFFICE
CERTIFICATE OF CORRECTION

PATENT NO.        : 7,060,104 B2                                            Page 1 of 1
APPLICATION NO.   : 10/410713
DATED             : June 13, 2006
INVENTOR(S)       : Van L. Phillips It is certified that error appears in the above-identified patent and that said Letters Patent is hereby corrected as shown below:

At column 1, line 38, please delete "Bladders"" and insert -- Bladders". --, therefor.

At column 2, line 9, please delete "foot-prosthesis" and insert -- foot prosthesis --, therefor.

At column 2, line 43, please delete "toe off" and insert -- toe-off --, therefor.

Signed and Sealed this

Twelfth Day of December, 2006

JON W. DUDAS
*Director of the United States Patent and Trademark Office*